(12) United States Patent
Gille et al.

(10) Patent No.: US 8,894,636 B2
(45) Date of Patent: Nov. 25, 2014

(54) MINIMALLY INVASIVE SURGICAL SYSTEM FOR $CO_2$ LASERS

(76) Inventors: Henrick K. Gille, Oceanside, CA (US);
Fritz A. Brauer, Oceanside, CA (US)

( * ) Notice: Subject to any disclaimer, the term of this patent is extended or adjusted under 35 U.S.C. 154(b) by 593 days.

(21) Appl. No.: 12/720,466

(22) Filed: Mar. 9, 2010

(65) Prior Publication Data
US 2011/0224661 A1    Sep. 15, 2011

(51) Int. Cl.
*A61B 17/00* (2006.01)
*A61B 18/04* (2006.01)
*A61B 18/18* (2006.01)

(52) U.S. Cl.
USPC ........... 606/16; 606/1; 606/2; 606/15; 606/33

(58) Field of Classification Search
USPC ....................................... 606/1, 2, 15, 16, 33
See application file for complete search history.

(56) References Cited

U.S. PATENT DOCUMENTS

| | | | |
|---|---|---|---|
| 4,917,083 A | 4/1990 | Harrington et al. | |
| 6,563,981 B2 | 5/2003 | Weisberg et al. | |
| 6,625,364 B2 | 9/2003 | Johnson et al. | |
| 6,728,439 B2 | 4/2004 | Weisberg et al. | |
| 6,788,864 B2 | 9/2004 | Ahmad et al. | |
| 6,801,698 B2 | 10/2004 | King et al. | |
| 6,879,386 B2 | 4/2005 | Shurgalin et al. | |
| 6,895,154 B2 | 5/2005 | Johnson et al. | |
| 6,898,359 B2 | 5/2005 | Soljacic et al. | |
| 6,903,873 B1 | 6/2005 | Joannopoulos et al. | |
| 7,072,553 B2 | 7/2006 | Johnson et al. | |
| 7,142,756 B2 | 11/2006 | Anderson et al. | |
| 7,167,622 B2 | 1/2007 | Temelkuran et al. | |
| 7,190,875 B2 | 3/2007 | Anderson et al. | |
| 7,231,122 B2 | 6/2007 | Weisberg et al. | |
| 7,331,954 B2 | 2/2008 | Temelkuran et al. | |
| 7,349,589 B2 | 3/2008 | Temelkuran et al. | |
| 2008/0215041 A1 | 9/2008 | Zemmouri et al. | |
| 2009/0018531 A1 | 1/2009 | Welches et al. | |
| 2009/0118715 A1* | 5/2009 | Mansour ........................ 606/4 |

OTHER PUBLICATIONS

ISR and WO for corresponding PCT/US2001/027454 mailed on Nov. 16, 2011.
BeamPath™ by OmniGuide Inc., http://www.omni-guide.com/beampath-technology-overview.htm.

* cited by examiner

*Primary Examiner* — Armando Rodriguez
(74) *Attorney, Agent, or Firm* — Stamoulis & Weinblatt LLC

(57) ABSTRACT

A Minimally Invasive Surgical Laser Hand-piece ("MISLH") for use with a probe is described. The MISLH has a MISLH proximal end and MISLH distal end, and the MISLH may include an optical coupler located at the MISLH proximal end, a substantially straight central bore within the MISLH, and an internal beam stop aperture within the central bore adjoined to the optical coupler. The central bore may extend from the optical coupler to the MISLH distal end and the central bore may be configured to accept the insertion of the probe within the central bore at the MISLH distal end. Additionally, the central bore may be configured to accept the insertion of the probe such that the probe is adjoined to the internal beam stop aperture.

18 Claims, 10 Drawing Sheets

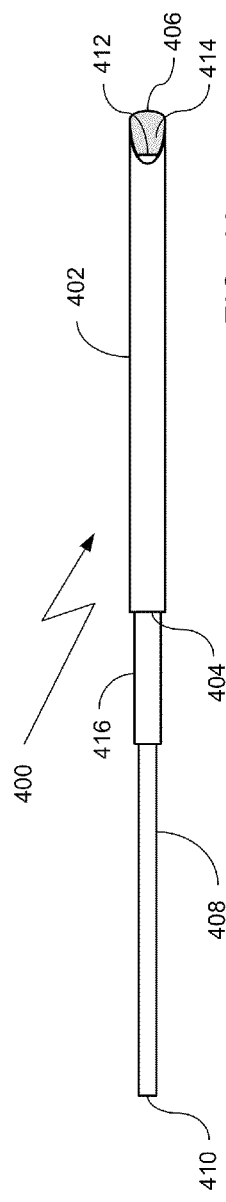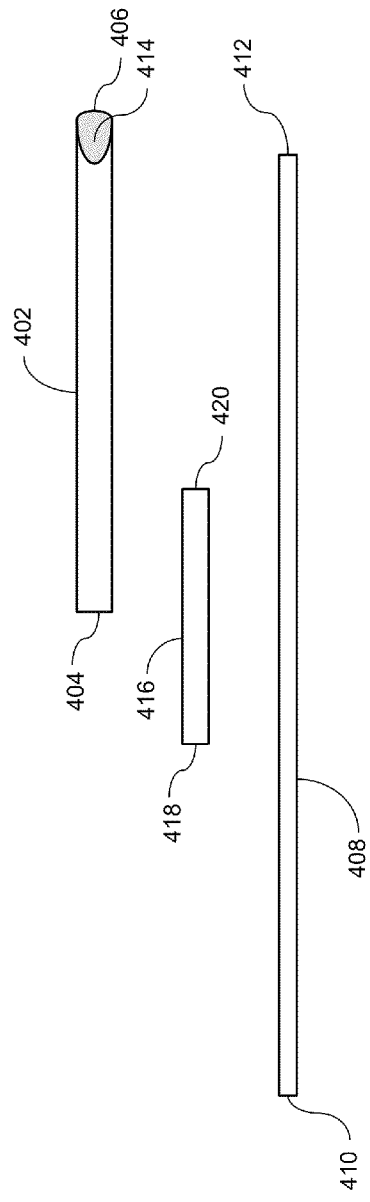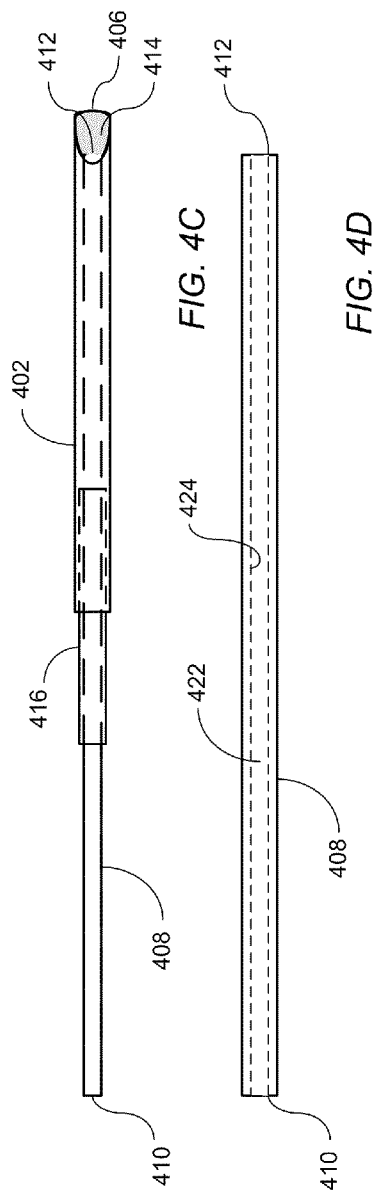
FIG. 4A
FIG. 4B
FIG. 4C
FIG. 4D

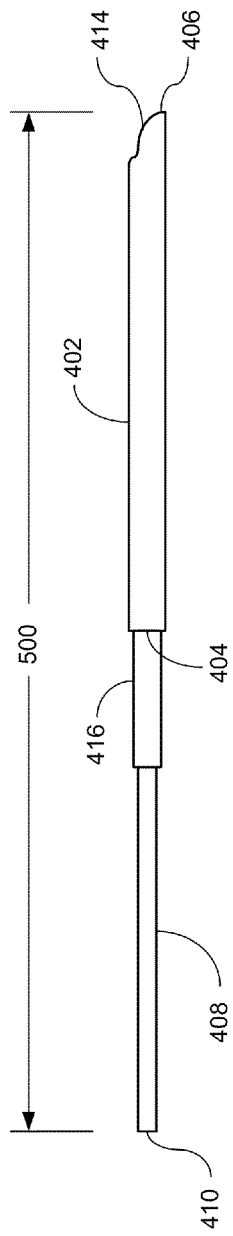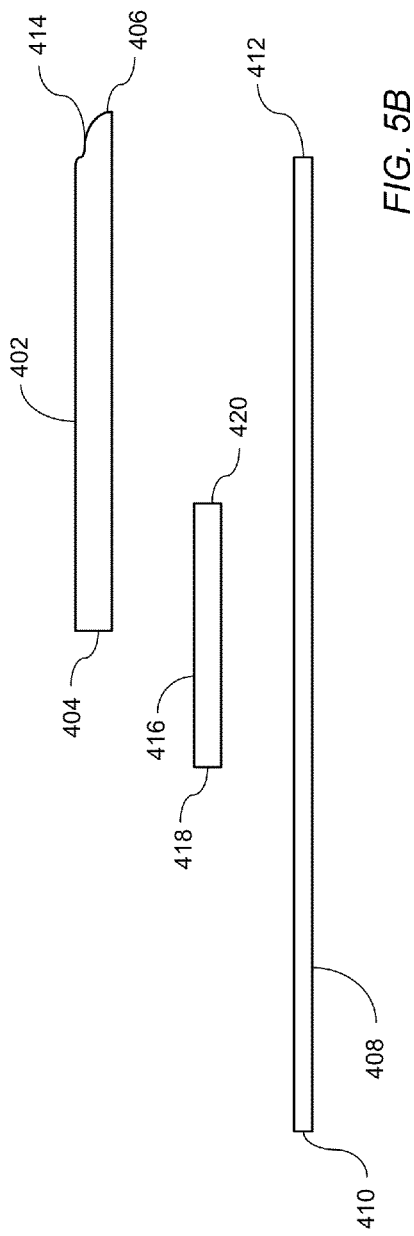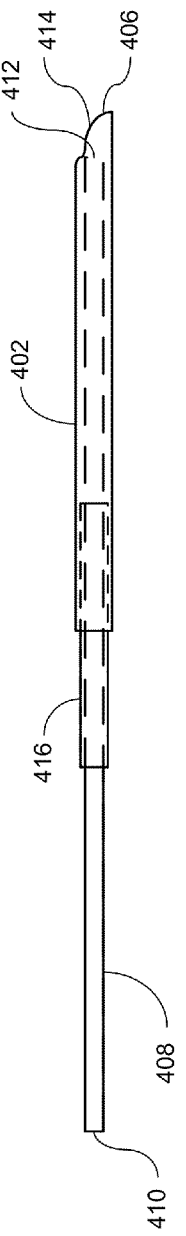
FIG. 5A
FIG. 5B
FIG. 5C

MINIMALLY INVASIVE SURGICAL SYSTEM FOR $CO_2$ LASERS

BACKGROUND OF THE INVENTION

1. Field of the Invention

This invention relates generally to the medical surgical field and, in particular, to the field of laser surgery.

2. Related Art

Surgical applications of lasers are well known in modern medicine. The types of lasers are nearly as numerous as the procedures that use them, and selection of a laser for any given procedure depends upon the laser-tissue interaction, which phenomena have been widely reported, and the desired outcome of that interaction. The types of lasers may be grouped into ultraviolet (193-351 nm), visible wavelength (400-700 nm), and infrared (700-100,000 nm) lasers.

Of the infrared lasers, the carbon dioxide ("$CO_2$") laser (with a wavelength of approximately 10.6 microns) is utilized most widely for surgical applications of ablation and cutting of tissue because the laser energy from a $CO_2$ laser can cut, cauterize and ablate human and animal tissue. Additionally, $CO_2$ lasers are also more readily available and more economical because they cost much less than other types of surgical lasers.

Moreover, the energy of a $CO_2$ laser is readily absorbed by water, which is the primary component of most biological tissue. This results in minimal thermal spread and makes $CO_2$ lasers very useful for applications near critical anatomical structures. As an example, a $CO_2$ laser's absorption in water is almost 400 times greater than that of an Argon laser.

Since approximately 60-70% of tissue is water, high absorption of $CO_2$ laser's energy in water implies that there will also be high absorption in tissue. This results in a superficial effect in which a $CO_2$ laser's energy is limited in its spread within a given target of tissue. Thus, a $CO_2$ laser has a superficial action limited to the upper layers of tissue when compared with other energy sources, and minimal damage to adjoining tissue volume. In addition, a $CO_2$ laser's energy seals small blood vessels as it cuts through the tissue rendering it an enhanced scalpel that combines precise cutting, ablation and microvascular coagulation while incurring minimal collateral thermal damage.

Unfortunately, while efficient optical waveguides (also known as fiber waveguides, fiber-optic waveguides, optical fibers, fibers, or lightpipes) exist for transmitting low amounts of energy particularly in the visible region, it is difficult to create an efficient waveguide, particularly a flexible waveguide, for transmitting relatively high amounts of energy, particularly in the infrared region, because of the lack of materials capable of efficiently transmitting power in this region. Specifically, a $CO_2$ laser cannot be delivered through quartz fiber optics, or silica or sapphire lenses, since these materials are opaque at the 10.6 micron wavelength. Materials that are commonly utilized with $CO_2$ laser light, both as lenses and as mirrors, include sodium chloride, potassium chloride, zinc selenide ("ZnSe"), and germanium. In early $CO_2$ laser designs, the $CO_2$ laser light was typically directed through a series of mirrors in a complex articulating system through which the light is delivered to a handpiece containing a lens which would allow the beam to be focused in a non-contact manner onto a target location.

As such, early $CO_2$ laser system included at least one $CO_2$ laser, an associated power supply, optical components (such as mirrors and lenses), and control electronics that occupy substantial space and floor area. This situation limited the application of $CO_2$ lasers somewhat in surgical applications.

Also, it is necessary to carry the laser light energy from the laser system into the surgical field—i.e., the place in the operating room where the patient, nurses and surgeon maintain a sterile environment. Sterility of laser surgical implements must be maintained so as to avoid nosocomial or other types of infections that could prove hazardous to the patient and his recovery from the surgical procedure.

As an example, these early $CO_2$ laser surgical systems included articulated optical arms with diagonal mirrors placed at rotating joints that were use to carry laser light energy through the arm to a surgical hand piece which included optics that focused the laser light energy so that the energy could be directed at tissue in the sterile surgical field. These articulated arms proved to be unergonomic and awkward to use, limited to "line-of-sight" surgical procedures, and they were too large for many surgical procedures performed in, for example, body cavities in the nose, bronchia, ears, or throat. As a result these systems fell into relative disuse because of these difficulties.

In order to overcome many of these problems, companies such as, for example, OmniGuide Inc. of Cambridge, Mass., developed novel small hollow core, thin, and flexible optical waveguides capable of delivering $CO_2$ laser energy through fibers mounted in handpieces attached to a variety of tips. Before utilizing this novel optical waveguide approach (such as, for example, BeamPath™ fibers produced by OmniGuide Inc.), conventional optical waveguides were used to guide laser light through solid core fibers via a process known as index guiding or total internal reflection. This form of transmission is dependent on the transparency of the material through which the light propagates, and thus carries with it all the limitations of the constituent material. As an example, the most acute limitation is that of light transmission across different wavelengths because, for example, silica's transmission window ranges from 300 nm to 2,000 nm, which is opaque to far infrared wavelengths.

Examples of these novel small hollow core, thin, and flexible optical waveguides include, for example, the BeamPath™ fibers produced by OmniGuide Inc., which are photonic bandgap fibers with each fiber having forty or more microscopic layers of alternating glass and polymer that form a reflective system known as a Bragg diffraction grating. The wavelength of light transmitted by this structure is a function of the thickness of the glass/polymer bi-layers, and may be varied.

These novel small hollow core, thin, and flexible optical waveguides are generally described by: U.S. Pat. No. 7,349,589, titled "Photonic Crystal Fibers and Medical Systems including Photonic Crystal Fibers," issued, Mar. 25, 2008, to Temelkuran et al.; U.S. Pat. No. 7,331,954, titled "Photonic Crystal Fibers and Medical Systems including Photonic Crystal Fibers," issued, Feb. 19, 2008, to Temelkuran et al.; U.S. Pat. No. 7,349,589, titled "Photonic Crystal Waveguides and Systems Using Such Waveguides," issued, Dec. 18, 2007, to Fink et al.; U.S. Pat. No. 7,231,122, titled "Photonic Crystal Waveguides and Systems Using Such Waveguides," issued, Jun. 12, 2007, to Weisberg et al.; U.S. Pat. No. 7,190,875, titled "Fiber Waveguide Formed From Chalcogenide Glass and Polymer," issued, Mar. 13, 2007, to Anderson et al.; U.S. Pat. No. 7,167,622, titled "Photonic Crystal Fibers and Medical Systems including Photonic Crystal Fibers," issued, Jan. 23, 2007, to Temelkuran et al.; U.S. Pat. No. 7,142,756, titled "High Index-Contrast Fiber Waveguides and Applications," issued, Nov. 28, 2006, to Anderson et al.; U.S. Pat. No. 7,072,553, titled "Low-Loss Photonic Crystal Waveguide Having Large Core Radius," issued, Jul. 4, 2006, to Johnson et al.; U.S. Pat. No. 6,903,873, titled "High Omnidirectional Reflector," issued, Jun. 7, 2005, to Joannopoulos et al.; U.S. Pat. No. 6,898,359, titled "High Index-Contrast Fiber Waveguides and Applications," issued, May 24, 2005, to Soljacic et al.; U.S. Pat. No. 6,895,154, titled "Photonic Crystal Optical Waveguides having tailored dispersion profiles," issued, May 17, 2005, to Johnson et al.; U.S. Pat. No. 6,879,386, titled "Optical Waveguide Monitoring," issued, Apr. 12, 2005, to Shurgalin et al.; U.S. Pat. No. 6,879,386, titled "Optical Waveguide Monitoring," issued, Nov. 9, 2004, to Shurgalin et al.; U.S. Pat. No. 6,801,698, titled "High Index-Contrast Fiber Waveguides and Applications," issued, Oct. 5, 2004, to King et al.; U.S. Pat. No. 6,788,864, titled "High Index-Contrast Fiber Waveguides and Applications," issued, Sep. 7, 2004, to Ahmad et al.; U.S. Pat. No. 6,728,439, titled "Electromagnetic Mode Conversion In Photonic Crystal Multimode Waveguides," issued, Apr. 27, 2004, to Weisberg et al.; U.S. Pat. No. 6,625,364, titled "Low-loss Photonic Crystal Waveguide Having Large Core Radius," issued, Sep. 23, 2003, to Johnson et al.; and U.S. Pat. No. 6,563,981, titled "Electromagnetic Mode Conversion In Photonic Crystal Multimode Waveguides," issued, May 13, 2003, to Weisberg et al., all of which are herein incorporated by reference in their entirety.

Unfortunately, while these novel small hollow core, thin, and flexible optical waveguides have advantages over the other known approaches in the prior art, this approach still suffers from several problems. As an example, in FIG. 1, a system diagram of an example of a known implementation of a small hollow core optical waveguide 100 is shown. The small hollow core optical waveguide 100 may include an outer tubular shell 102 having a distal end 104 and hollow core 106, where the hollow core (also known as a central lumen) 106 and outer tubular shell 102 define an outer lip 108 at the distal end 104. In an example of operation, the small hollow core optical waveguide 100 receives $CO_2$ laser energy at an input (not shown) to the small hollow core optical waveguide 100 and, in response, produces an output laser beam 110 that exits the distal end 104 in an axial direction 112 with a fan shaped energy distribution. In FIG. 1, the output laser beam 110 is shown having an initial radius 114 at the distal end 104 and then three stop sizes 116, 118, and 120 that increase in radius 122, 124, and 126, respectively, as the distance 128, 130, and 132, respectively, from the distal end 104 is increased. The output laser beam 110 has a fan shaped energy distribution because the small hollow core optical waveguide 100 is not a mode preserving device—i.e., it does not preserve the Gaussian energy distribution of a $TEM_{00}$ laser beam.

This presents several practical problems to a surgeon attempting to use this small hollow core optical waveguide 100 for surgery because precise surgery in small body cavities, on small structures of tissue, depends upon precisely positioning the laser beam 110 and moving it over the tissue in an accurate fashion so as to cut or ablate tissue. With the small hollow core optical waveguide 100, shown in FIG. 1, this is very difficult because the sharpest part of the laser beam 110 is closest to the distal end 104 of the small hollow core optical waveguide 100. This means that the surgeon must attempt to keep the laser beam 110 at a close and uniform distance from the tissue (not shown). This distance is very difficult to control with a hand-held probe being used in small confined body cavities. When a surgeon cuts using the prior art waveguide 100 he, or she, is in danger of varying the cut width causing areas of cauterization, and ablation creating a jagged rough edge that may have areas of charred or carbonized tissue. This occurs because as the distance from the tissue to the laser beam 110 varies, the energy delivered to the tissue varies and can diverge to the point of charring tissue instead of ablating tissue.

As a practical matter, the prior art waveguides (such as the small hollow core optical waveguide 100) need to be cooled by blowing air or gas through the central lumen of the waveguide during surgery because the dielectric coating in the waveguide is "lossy" and it is not an efficient reflector of $CO_2$ laser light energy which causes the waveguide to heat up. In a typical surgery, the waveguide is often bent, and if too severely bent, may result in the laser beam burning through the sidewall of the waveguide causing catastrophic failure, stopping the surgery until the waveguide is replaced, lengthening the patient's exposure to anesthesia, and creating general inconvenience for the surgical staff.

Another disadvantage of the waveguide 100 design is that a diverging laser beam 110 would require intermediate optical lenses if the waveguide 100 is to be joined or extended. Lenses are not desirable for $CO_2$ laser light, because of their transmission losses and they are generally composed of toxic materials such as ZnSe.

Because the fiber must be continuous, without junctions or breaks in the waveguide from the laser to the surgical handpiece, the surgical probe designs are limited to hollow tubes that require insertion of the waveguide in order to create a usable surgical instrument.

As such, there is a need for a $CO_2$ laser surgical system that solves the above mentioned problems.

SUMMARY

A Minimally Invasive Surgical Laser Hand-piece ("MISLH") for use with a probe is described. The MISLH has a MISLH proximal end and MISLH distal end, and the MISLH may include an optical coupler located at the MISLH proximal end, a substantially straight central bore within the MISLH, and an internal beam stop aperture within the central bore adjoined to the optical coupler. The central bore may extend from the optical coupler to the MISLH distal end and the central bore may be configured to accept the insertion of the probe within the central bore at the MISLH distal end. Additionally, the central bore may be configured to accept the insertion of the probe such that the probe is adjoined to the internal beam stop aperture.

The probe may be a Minimally Invasive Surgical Laser Probe ("MISLP"). The MISLP may include a probe head that includes a probe head proximal end and a probe head distal end. The MISLP may also include a probe waveguide that protrudes from the probe head proximal end, where the probe waveguide is configured to be inserted within the central bore of the MISLH.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

FIGS. 4A, 4B, and 4C are bottom views of an example of an implementation of the MISLP in accordance with the invention.

FIG. 4D is top view of an example of an implementation of the probe waveguide shown in FIGS. 4A, 4B, and 4C.

FIGS. 5A, 5B, and 5C are side views of the MISLP shown in FIGS. 4A, 4B, and 4C.

DETAILED DESCRIPTION

A Minimally Invasive Surgical Laser System ("MISLS") is described that includes a Minimally Invasive Surgical Laser Hand-piece ("MISLH") and a Minimally Invasive Surgical Laser Probe ("MISLP"). The MISLH is a hand-piece described for use with a probe. The MISLH has a MISLH proximal end and MISLH distal end, and the MISLH may include an optical coupler located at the MISLH proximal end, a substantially straight central bore within the MISLH, and an internal beam stop aperture within the central bore adjoined to the optical coupler. The central bore may extend from the optical coupler to the MISLH distal end and the central bore may be configured to accept the insertion of the probe within the central bore at the MISLH distal end. Additionally, the central bore may be configured to accept the insertion of the probe such that the probe is adjoined to the internal beam stop aperture.

The probe may be the MISLP. The MISLP may include a probe head that includes a probe head proximal end and a probe head distal end. The MISLP may also include a probe waveguide that protrudes from the probe head proximal end, where the probe waveguide is configured to be inserted within the central bore of the MISLH.

Figure 1:
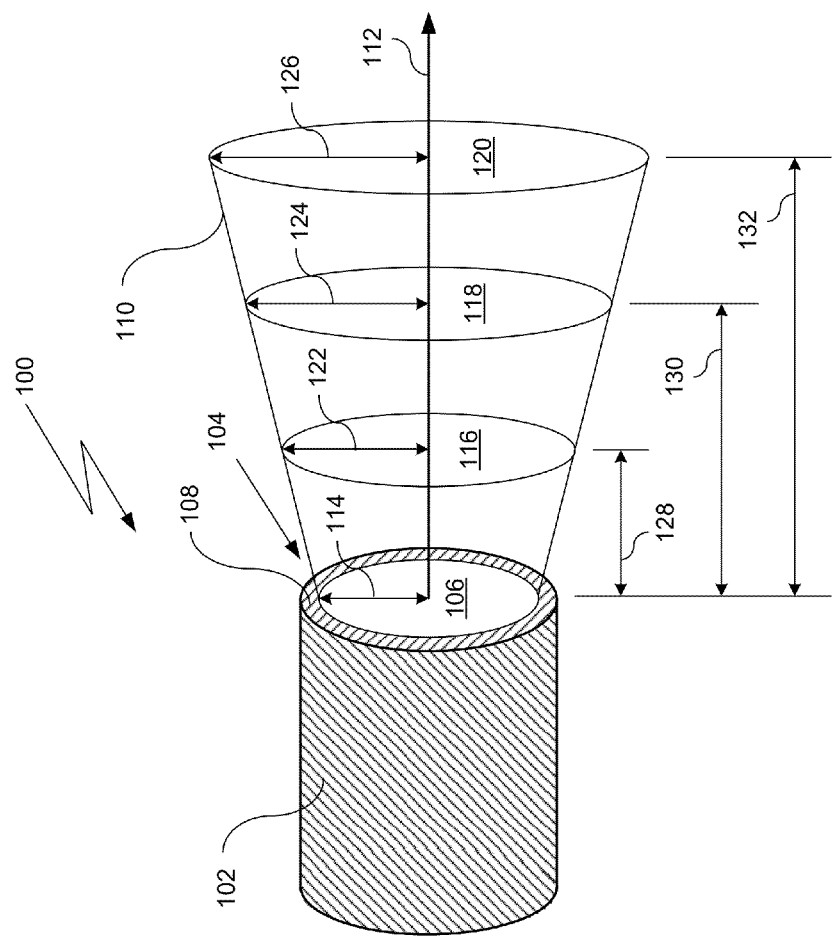
FIG. 1 a system diagram of a known example of an implementation of a small hollow core optical waveguide.
Figure 2:
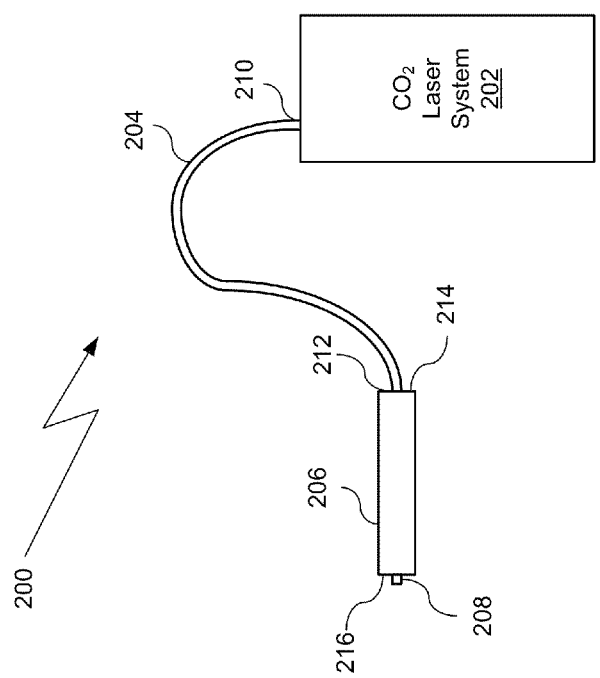
FIG. 2 is a system diagram of an example of an implementation of a Minimally Invasive Surgical Laser System ("MISLS") having a Minimally Invasive Surgical Laser Hand-piece ("MISLH") and a Minimally Invasive Surgical Laser Probe ("MISLP") in accordance with the invention.

In FIG. 2, a system diagram of an example of an implementation of a MISLS 200 is shown in accordance with the invention. The MISLS 200 may include a $CO_2$ laser system 202, a flexible hollow waveguide 204, a MISLH 206, and a MISLP 208. In this example, flexible hollow waveguide 204 has flexible hollow waveguide proximal end 210 and a flexible hollow waveguide distal end 212. Similarly, the MISLH 206 has a MISLH proximal end 214 and a MISLH distal end 216. The flexible hollow waveguide proximal end 210 is in signal communication with the $CO_2$ laser system 202 and the flexible hollow waveguide distal end 212 is in signal communication with the MISLH proximal end 214. The MISLP 208 is partially disposed within the MISLH 206 and extends out from the MISLH distal end 216.

The $CO_2$ laser system 202 is a system capable of producing $CO_2$ laser light energy at a wavelength of approximately 10.6 micrometers and output power levels of 0 to 50 Watts. The flexible hollow waveguide 204 includes a hollow tube of flexible, thin-wall silica-glass tube with a protective sheath on its outer surface. The inner surface of the tube is coated with a material, such as silver, that is optically reflective at infrared wavelengths. Additionally, a dielectric film, such as silver iodide, may be deposited on the reflective layer. As an example, the flexible hollow waveguide 204 may be constructed according to the disclosures of U.S. Pat. No. 5,567,471, titled "Coherent, Flexible, Coated-Bore Hollow-Fiber Waveguide, And Method of Making Same," which issued on Oct. 22, 1996 to Harrington, et al. and U.S. Pat. No. 5,567,471, titled "Coherent, Flexible, Coated-Bore Hollow-Fiber Waveguide," which issued on Aug. 8, 1995 to Harrington, et al., both of which are incorporated herein by reference in their entirety.

As an example of operation, $CO_2$ laser system 202 produces laser energy that is transmitted along the flexible hollow waveguide 204 to the MISLH 206. The MISLH 206 then transmits the received laser energy from the flexible hollow waveguide 204 to the MISLP 208, which outputs a laser beam.

Figure 3:
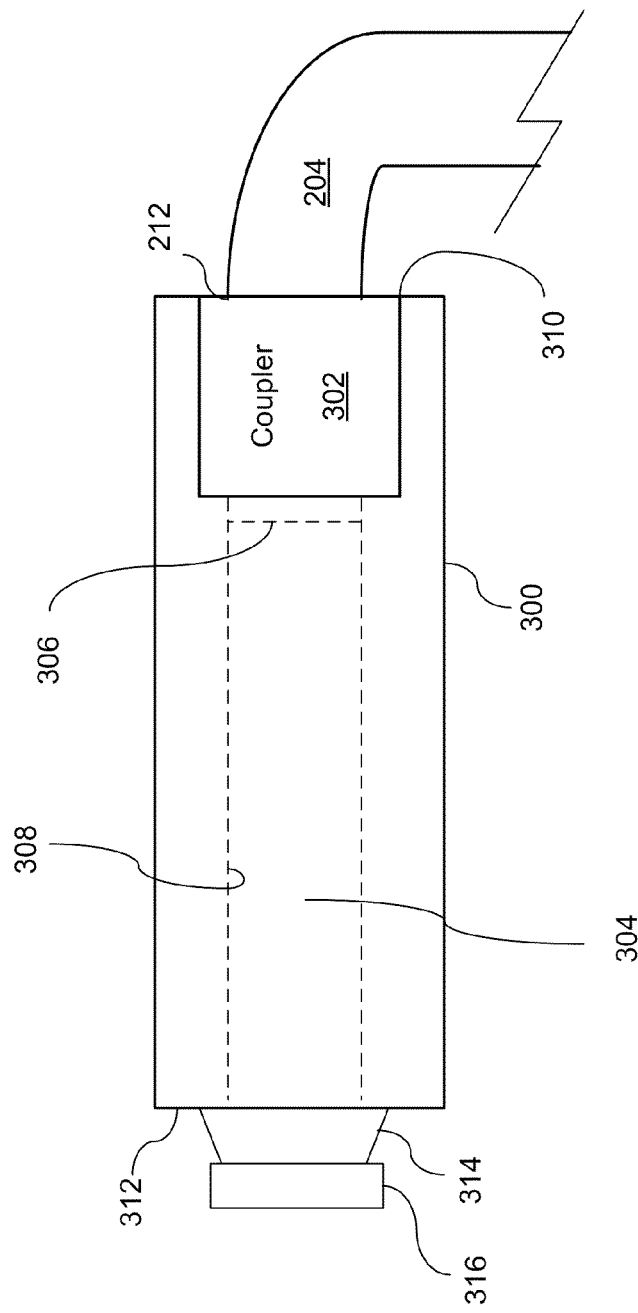
FIG. 3 is a side view of an example of an implementation of the MISLH in accordance with the invention.

In FIG. 3, a side view of an example of an implementation of the MISLH 300 is shown in accordance with the invention. The MISLH 300 may include an optical coupler 302, a substantially straight central bore 304 within the MISLH 300, and an internal beam stop aperture 306. The MISLH 300 has a MISLH proximal end 310 and a MISLH distal end 312 and the optical coupler 302 is located at the MISLH proximal end 310. The central bore 304 has an internal surface 308 and the central bore 304 extends from the optical coupler 302 to the MISLH distal end 312. The internal beam stop aperture 306 is located within the central bore 304 and is adjoined to the optical coupler 302. The optical coupler 302 is in signal communication with the flexible hollow waveguide 204 at the MISLH proximal end 310. The central bore 304 is configured to accept the insertion of the MISLP (such as MISLP 208 shown in FIG. 2) within the central bore 304 at the MISLH distal end 312. The MISLH 300 may include a collet 314 at the MISLH distal end 312 and a nosepiece 316 that is adjacent the collet 314 where the nosepiece 316 may be threaded onto the collet 314. The collet 314 and nosepiece 316 act together as a holding device that forms a collar around the MISLP, once inserted in the central bore 304. The collet 314 exerts a strong clamping force on the MISLP when it is tightened via the nosepiece 316. In this example, the MISLH 300 and collet 314 may be constructed from one of a number of materials such as, for example, aluminum, titanium, chrome plated brass, and/or anodized aluminum.

It is appreciated by those skilled in the art that the term "in signal communication" means that two or more devices and/or components are capable of communicating with each other via signals that travel over some type of signal path. The signals may be communication, power, or energy signals which may transmit communicate information, power, and/or energy from a first device and/or component to a second device and/or component along a signal path between the first device and/or component and second device and/or component. The signal paths may include physical, electrical, magnetic, electromagnetic, optical, electrochemical, wired, and/ or wireless connections between the first device and/or component and second device and/or component. The signal paths may also include additional devices and/or components between the first device and/or component and second device and/or component.

In FIG. 4A, a bottom view of an example of an implementation of the MISLP 400 is shown in accordance with the invention. The MISLP 400 may include a probe head 402, with a probe head proximal end 404 and a probe head distal end 406, and a probe waveguide 408 that protrudes from the probe head proximal end 404. The probe waveguide 408 also has a probe waveguide proximal end 410 and a probe waveguide distal end 412, where the probe waveguide distal end 412 is located close to the probe head distal end 406. The probe head 402 may include a scalloped portion 414 at the probe head distal end 406. The probe head 402 may be an outer tube that establishes an insertion distance into the MISLH 300 (of FIG. 3). The MISLP 400 may also include a probe inner tube 416 that extends over the probe waveguide 408 that protects and adds rigidity to the probe waveguide 408. The probe head 402 may be constructed of numerous materials such as, for example, a metal (such as, for example, aluminum, stainless steel), nitinol, or polyimide. Similarly, the probe inner tube 416 may also be constructed of same type of materials as the probe head 402. In this example, the probe waveguide 408 may be recessed by about 1 millimeter from the probe head distal end 406 into the probe head 402.

In FIG. 4B, the probe head 402 (i.e., a probe "tip"), probe waveguide 408, and probe inner tube 416 are shown separately. The probe inner tube 416 (also known as a probe "sleeve") may include a probe inner tube proximal end 418 and probe inner tube distal end 420. The probe waveguide distal end 412 is inserted through the probe inner tube proximal end 418, through the probe inner tube 416, out the probe inner tube distal end 420 and into the probe head 402. The probe waveguide distal end 412 may be flush with, extend beyond, or recess behind the probe head distal end 406. If the probe waveguide distal end 412 is recessed behind the probe head distal end 406, the probe head 402 may be scalloped (with a scalloped portion 414) at the probe head distal end 406.

In FIG. 4C, the probe head 402, probe waveguide 408, and probe inner tube 416 are shown assembled with phantom lines showing how the probe inner tube 416 extends into the probe head 402 and how the probe waveguide 408 extends through probe inner tube 416 and substantially all of the probe head 402.

In FIGS. 4A, 4B, and 4C, and 4D, the probe waveguide 408 is configured to be inserted into the central bore 304 of the MISLH 300. The probe waveguide 408 has a hollow lumen 422 that extends from the probe waveguide proximal end 410 to the probe waveguide distal end 412 and has a lumen inner surface 424. In general, the probe waveguide 408 may contain a hollow glass capillary tube with an outer coating of acrylic plastic sleeving (not shown) that serves as a stiffener. The inner bore of the capillary tube is coated in accordance with the coating process described by U.S. Pat. Nos. 5,567,471 and 5,567,471 to Harrington, et al. creating an optical waveguide with mode preserving properties. As an example, the acrylic plastic sleeving at the probe waveguide proximal end 410 may be removed for a distance of approximately 0.04 to 0.06 inches to prevent glass particles from being retained by the acrylic if the glass capillary is cleaved.

In FIG. 5, a side view is shown of the MISLP 400 shown in FIGS. 4A, 4B, and 4C. The probe head 402 may alternatively have numerous types of shapes (such as, for example, square cut across the fiber, scalloped tips and/or user shaped probes) based on the type of surgery for which the probe head 402 will be used such as, for example, penetrating through small openings and channels. Table 1, below, summarizes some example types of MISLP. The MISLPs may vary in length 500, outer sleeving material of probe inner tube 416, degree of rigidity or flexibility, curved, straight, user adjustable curvature, and distal end tip configuration of the probe head 402.

TABLE 1

For The MISLP

| Surgical Specialty | Probe Head Configuration | Probe Sleeve Material | MISLP Length | Probe Head Distal End Configuration |
| --- | --- | --- | --- | --- |
| Dissection | Straight | SS 304 14GA | 1.5 to 9.5 inches | Scalloped |
| ENT | 1 Bend R = 0.75" | SS 304 14GA | 2.0 inches | Scalloped |
| ENT | 1 Bend R = 1.00" | SS 304 14GA | 3.0 inches | Scalloped |
| ENT | 1 Bend R = 1.00" | SS 304 14GA | 9.5 inches | Scalloped |
| ENT | Straight | SS 304 14GA | 2.0 inches | Scalloped |
| ENT | Straight | SS 304 14GA | 3.0 inches | Scalloped |
| ENT | 2 Bend R = 1.00" & 0.75" | SS 304 14GA | 9.5 inches | Scalloped |
| Neuro | Straight | SS 304 14GA | 1.5 inches | Scalloped |
| Neuro | Straight | SS 304 14GA | 2.0 inches | Scalloped |
| Neuro | Straight | SS 304 14GA | 3.0 inches | Scalloped |
| ENT | User Bendable | Al 3003 14 GA | 3.0 to 9.5 inches | Scalloped |
| ENT, Pediatric and Adult Bronchoscopy | Flexible | Polyimide 17 GA | 3.0 to 6.0 inches | Flat |
| Stapedectomy, Myringotomy | Straight | Polyimide 17 GA | 3.0 to 6.0 inches | Flat |
| Stapedectomy | Straight | Polyimide 23 GA | 3.0 inches | Flat |

In Table 1, "SS" means stainless steel, "ENT" stands for Ear Nose Throat, and "Neuro" refers to Neurological surgical specialties.

Figure 6:
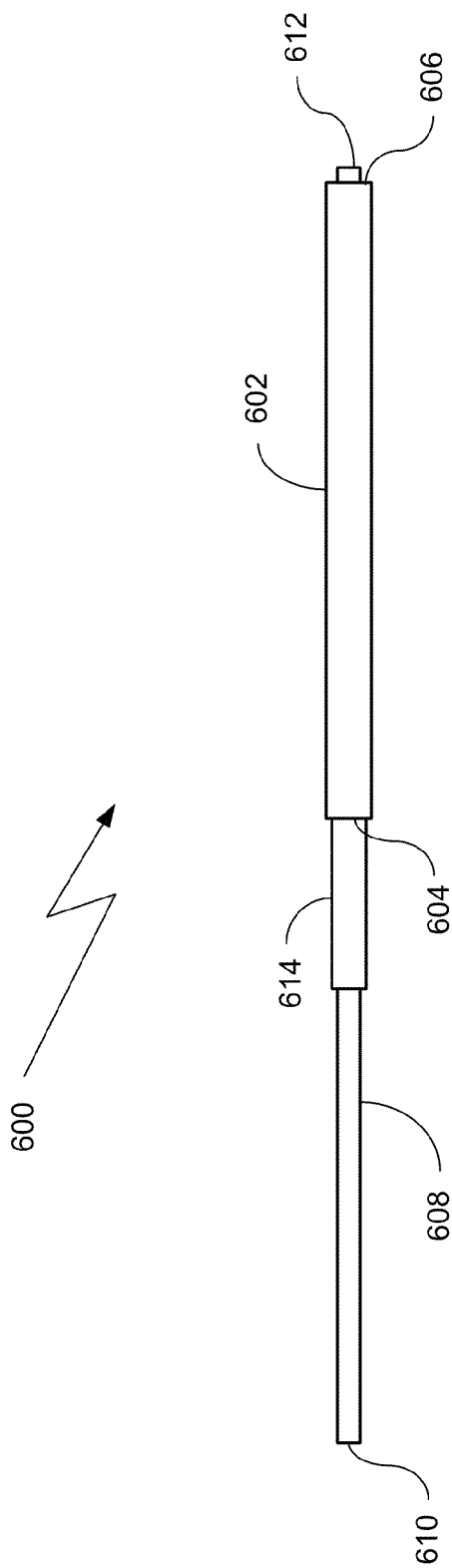
FIG. 6 is a side view of an example of another implementation of the MISLP in accordance with the invention.

In FIG. 6, a side view of an example of another implementation of the MISLP 600 is shown in accordance with the invention. The MISLP 600 may include a probe head 602, with a probe head proximal end 404 and a probe head distal end 606, and a probe waveguide 408 that protrudes from the probe head proximal end 604 and probe head distal end 606. The probe waveguide 608 also has a probe waveguide proximal end 610 and a probe waveguide distal end 612, where the probe waveguide distal end 612 is located close to the probe head distal end 606. Unlike the example in FIGS. 4A, 4B, and 4C, and 4D, the probe head 602 does not include a scalloped portion at the probe head distal end 606 because the probe waveguide 608 extends from the probe head distal end 606. Similar to example above, the probe head 602 may be an outer tube that establishes an insertion distance into the MISLH 300 (of FIG. 3). The MISLP 600 may also include a probe inner tube 614 that extends over the probe waveguide 608 that protects and adds rigidity to the probe waveguide 608. The probe head 602 may be constructed of numerous materials such as, for example, stainless steel or polyimide.

Figure 7:
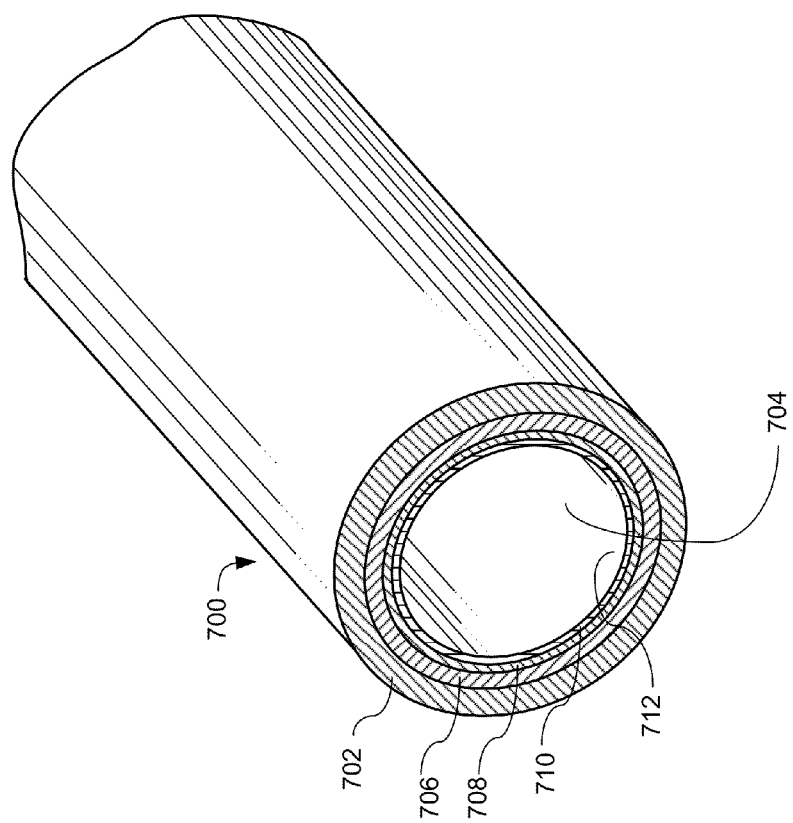
FIG. 7 is a front prospective view of an example of an implementation of a probe waveguide in accordance with the invention.
Figure 8:
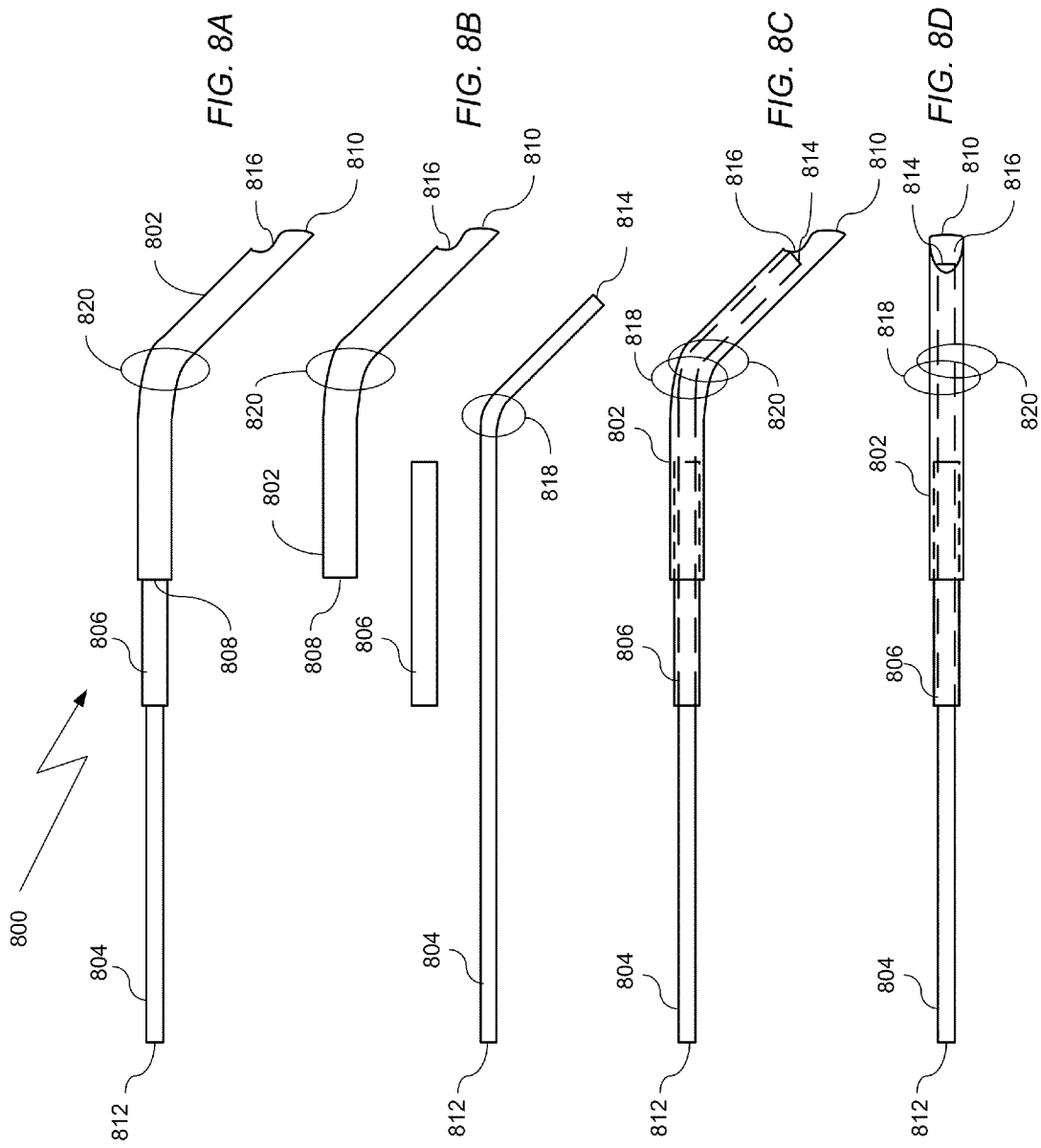
FIGS. 8A, 8B, are 8C are side views of another example of an implementation of the MISLP in accordance with the invention.
FIG. 8D is top view of an example of an implementation of the MISLP shown in FIGS. 8A, 8B, and 8C.

Turning to FIG. 7, a front prospective view is shown of an example of an implementation of the probe waveguide 700 in accordance with the invention. As an example, similar to the flexible waveguide 204, the probe waveguide 700 may be constructed according to the disclosures of U.S. Pat. Nos. 5,567,471 and 5,567,471 to Harrington, et al. Specifically, the probe waveguide 700 may include a protective sheath 702 (which may be a polymer coating, polyimide, silicone, nylon, metal or other material) which is formed around or onto the outer surface of the barrel of a hollow-fiber waveguide having a smooth bore (i.e., hollow lumen 704), such as a commercially available, thin-wall silica-glass tubing 706. The sheath 702 protects the tubing 706 from abrasion and other mechanical degradation and seals against moisture and other substances that may physically degrade the tubing 706.

The probe waveguide 700 also includes a reflective layer 708 that is deposited onto the bore of the tubing 706 in such a way as to retain a smooth exterior surface for the reflective layer 708 or such that the reflective layer 708 "levels" to a smooth reflective surface. As an example, the reflective layer 708 may be silver of less than 1 µm in thickness. As another example, the reflective layer 708 may be a metal (such as, for example, gold, copper, aluminum, platinum, molybdenum, zinc, and nickel) and/or a semiconductor (such as, for example, germanium, etc.).

The probe waveguide 700 may also include a dielectric film 710 having an index of refraction that is less than the index of refraction of the reflective layer 708. The dielectric film 710 is generally fabricated or deposited (i.e., "created") on the bore of the reflective layer 708 in a manner that substantially retains or improves the smoothness of the exposed surface of the bore. The dielectric film 710 enhances the reflectively of the inner exposed surface 712 of the bore 704 of the probe waveguide 700. The thickness of the dielectric film 710 is generally determined by optical measurements and is controlled to give the lowest loss at a particular infrared wavelength. As an example, the dielectric film 710 is approximately 0.1 µm to 0.8 µm thick. The dielectric film 710 may be silver iodide or an inorganic compound (such as, for example, silver bromide, copper iodide, copper selenide, silver sulfide, zinc selenide, and zinc sulfide).

The inner exposed surface 712 of the dielectric film 710 defines the bore 704 as a hollow interior volume (i.e., a hollow lumen), of the probe waveguide 700, which may contain air, another gas or gaseous mixture, or any other medium preferably having an index of refraction that is approximately equal to 1. The reflective layer 708 and the dielectric film 710 may be thin and flexible so that the probe waveguide 700 may be a flexible tube with special coatings deposited on the bore to produce a very low loss waveguide at infrared wavelengths.

As an example, the internal diameter of the probe waveguide 700 prior to the application of the reflective layer 708, may be from less than about 100 micrometers to about 1600 micrometers. The smoothness of the bore of the tubing 706 prior to finishing may be about 0.05 micrometers or less, where the finished probe waveguide 700 preferably has a similar degree of smoothness because such smoothness contributes substantially to the high performance characteristics of the present invention.

The spatial profile of the laser beam (not shown) that is output at the probe waveguide distal end 412, made in accordance with the present invention, depends upon the diameter of the hollow lumen 704 of the probe waveguide 408, the purity of the input laser beam (not shown), and is somewhat affected by the bending radius of the probe waveguide 408 (assuming that the probe waveguide 408 is not substantially straight). Thus, the spatial profile of the laser beam output at the probe waveguide distal end 412 is more similar to the spatial profile of the laser beam input at the probe waveguide proximal end 410—i.e., the laser beam conduction method through the probe waveguide 408 preserves the essential energy distribution of the laser beam which is generally known as "mode preservation" by those skilled in the art. This is due to the fact that a smaller hollow lumen 704 causes higher loss for high-order modes than for lower-order modes. Waveguides having a relatively small hollow lumen 704 (for example, approximately 0.5 mm) will best preserve the TEM % mode that is launched into the waveguide at the proximal end of the waveguide.

In an example of operation, the power/energy that is input at the probe waveguide proximal end 410 from a $TEM_{00}$ Gaussian laser beam source propagates along the probe waveguide 408 with low attenuation in a nearly $HE_{11}$ fiber eigenmode to the probe waveguide distal end 412. At the probe waveguide distal end 412, the power/energy is emitted as if it were merely the continuation, without significant degradation, of the input $TEM_{00}$ eigenmode. Since the laser beam emitted from the probe waveguide distal end 412 is a $TEM_{00}$ Gaussian laser beam is without significant power degradation, no cooling gas is needed with the present invention.

It is appreciated by those skilled in the art, that the same type of waveguide structure utilized and described above for the probe waveguide 408 may also be utilized for the flexible hollow waveguide 204. The only difference is that the waveguide structure for the probe waveguide 408 is designed to be more rigid and not as flexible as the flexible hollow waveguide 204 such that the probe waveguide 408 fits snuggly and securely into the central bore 304 of the MISLH 300. However, it is appreciated by those skilled in the art, that described waveguide structure for the probe waveguide 408 can be configured by inserting the waveguide in tubing made from stainless steel, aluminum, etc and that this tubing can be bent, bending the waveguide 408 without degrading the transmitted laser beam within the probe waveguide 408.

Similarly to FIGS. 5A, 5B, and 5C, FIGS. 8A, 8B, and 8C are side views of an example of another implementation of the MISLP 800 in accordance with the invention. Similar to FIGS. 5A, 5B, and 5C, the MISLP 800 may include a probe head 802, a probe waveguide 804, and a probe sleeve (i.e., probe inner tube) 806. The probe head 802 has a probe head proximal end 808 and a probe head distal end 810, and the probe waveguide 804 protrudes from the probe head proximal end 808. The probe waveguide 804 also has a probe waveguide proximal end 812 and a probe waveguide distal end 814, where the probe waveguide distal end 814 is located close to the probe head distal end 810. Similar to the example in FIGS. 4A, 4B, and 4C, the probe head 802 may include a scalloped portion 816 at the probe head distal end 810. Again, the probe head 802 may be an outer tube that establishes an insertion distance into the MISLH 300 (of FIG. 3). The probe sleeve 806 may extend over the probe waveguide 804 that protects and adds rigidity to the probe waveguide 804. The probe head 802 may be constructed of numerous materials such as, for example, a metal (such as, for example, aluminum, stainless steel), nitinol, or polyimide. Similarly, the probe sleeve 806 may also be constructed of the same type of materials as the probe head 802. In this example, the probe waveguide 804 may be recessed by about 1 millimeter from the probe head distal end 810 into the probe head 802. In FIG. 8D, a top view the MISLP 800 is shown.

The probe waveguide 804 is configured to be inserted into the central bore 304 of the MISLH 300. The probe waveguide 804 has a hollow lumen (not shown) that extends from the probe waveguide proximal end 812 to the probe waveguide distal end 814 and has a lumen inner surface (not shown). Unlike the MISLP 400, shown in FIGS. 4A, 4B, 4C, 5A, 5B, 5C, and 6, the MISLP 800 of FIG. 8 includes a bend 818 in the probe waveguide 804. By having a bend 818, the probe waveguide 804 may be designed to have physical configuration that is more convenient for a surgeon to use in a particular type of surgery. Correspondingly, the probe head 802 also has a bend 820 that corresponds to the probe waveguide bend 818. Examples of surgical specialties suited to a particular probe type are described above in Table 1. While the probe waveguide distal end 814 is shown as recessed within the scalloped portion 816 at the probe head distal end 810, similar to the example shown in FIG. 6, it is appreciated that that the probe waveguide distal end 814 may alternatively be flush with or extend beyond the probe head distal end 810.

Figure 9:
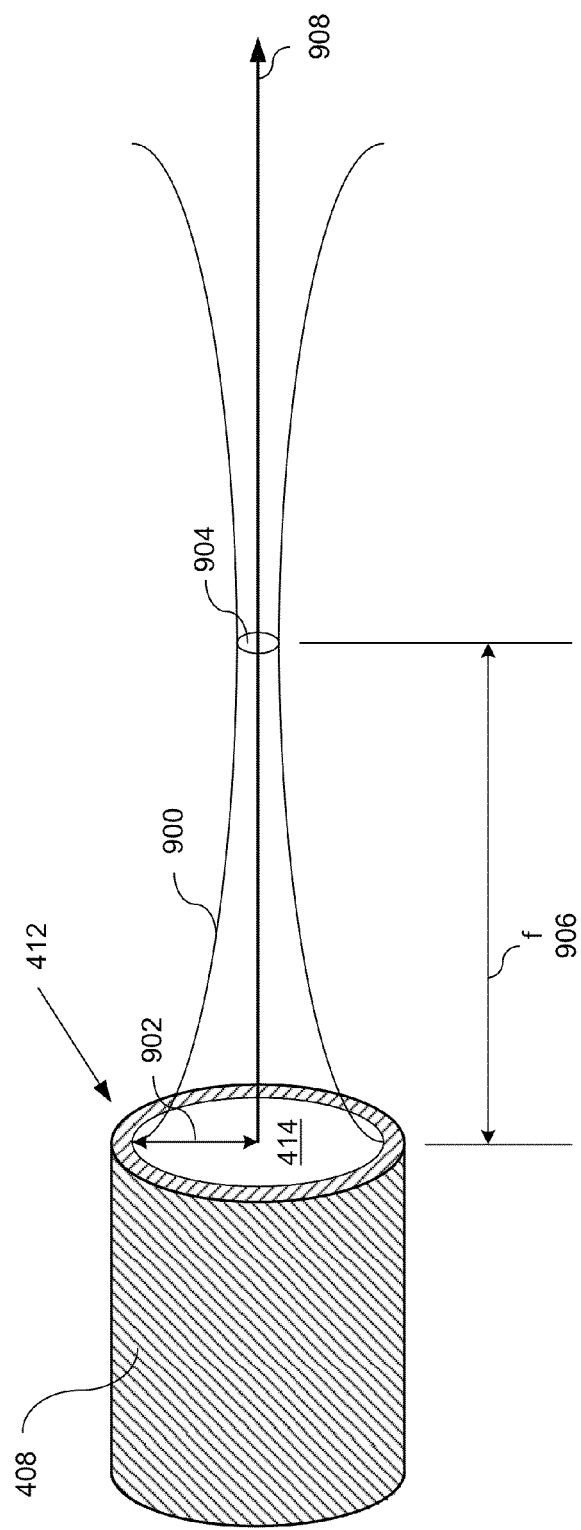
FIG. 9 is a system diagram of an example of an implementation of the operation of the probe waveguide (or flexible hollow waveguide).

Turning to FIG. 9, a system diagram of an example of an implementation of the operation of the probe waveguide 408 (or flexible hollow waveguide 204) is shown. The laser beam spatial profile 900 of laser beam of the laser beam as the laser beam exits the hollow lumen 414 at the probe waveguide distal end 412 is shown in FIG. 9. This laser beam spatial profile 900 is the result of the laser beam being a Gaussian beam.

In general for a Guassian beam, the complex electric field amplitude as a function of radial distance r, and axial length z is give by the following relationship:

$$E(r, z) = E_0 \frac{\omega_0}{\omega(z)} e^{\left(\frac{-r^2}{\omega^2(z)}\right)} e^{\left(-ikz - ik\frac{r^2}{2R(z)} + i\zeta(z)\right)},$$

where
 r 902 is the radial distance from the center axis of the beam,
 z is the axial distance from the beam's narrowest point (the "waist" 904),
 i is the imaginary unit (for which $i^2 = -1$), $$k = \frac{2\pi}{\lambda}$$

is the wave number in radians per meter,
 $E_0 = |E(0,0)|$,
 $\omega(z)$ is the radius at which the field amplitude and intensity drop to $1/e$ and $1/e^2$ of their axial values, respectively, and
 $\omega_0 = \omega(0)$ is the waist size (i.e., the radius of the waist 904). The functions $\omega(z)$, $R(z)$, and $\zeta(z)$ are parameters of the Gaussian beam that are also known as the beam width or "spot size," the radius of curvature, and Gouy phase, respectively.

For a Gaussian beam propagating in free space, the spot size $\omega(z)$ will be at a minimum value $\omega_0$ at one place a distance "f" 906 from probe waveguide distal end 412 along the beam axis 908, known as the beam waist 904. For a beam of wavelength λ at a distance z along the beam from the beam waist 904, the variation of the spot size is given by $$\omega(z) = \omega_0 \sqrt{1 + \left(\frac{z}{z_R}\right)^2},$$

where the origin of the z-axis 908 is defined, without loss of generality, to coincide with the beam waist 904, and where $$z_R = \frac{\pi \omega_0^2}{\lambda}$$

is called the Rayleigh range. The radius of curvature R(z) of the wavefronts comprising the beam is a function of position and is $$R(z) = z\left[1 + \left(\frac{z_R}{z}\right)^2\right].$$

The longitudinal phase delay (known as the Gouy phase) of the beam is defined by $$\zeta(z) = \arctan\left(\frac{z}{z_R}\right).$$

As the beam continues along the z-axis 908 the beam will begin to diverge from the beam waist 904. These parameters are well known to those skilled in the art such that their extensive descriptions need not be described here.

Through the proper design of these parameters it is possible to design the probe head 402 and probe waveguide 408 such that the length f 906 to the beam waist 904 may correspond to the length of the probe head 402 from the probe head proximal end 404 to the probe head distal end 406 or a minimum of the length of the probe head 402 from the probe head proximal end 404 to approximately 1.5 mm from the probe end 406 (i.e., the probe tip). As an example, the scalloped portion (both 414 in FIG. 4 and 816 in FIG. 8) may be utilized to establish the distance from the waveguide distal end (412 or 810) to the tissue (not shown) being ablated.

Figure 10:
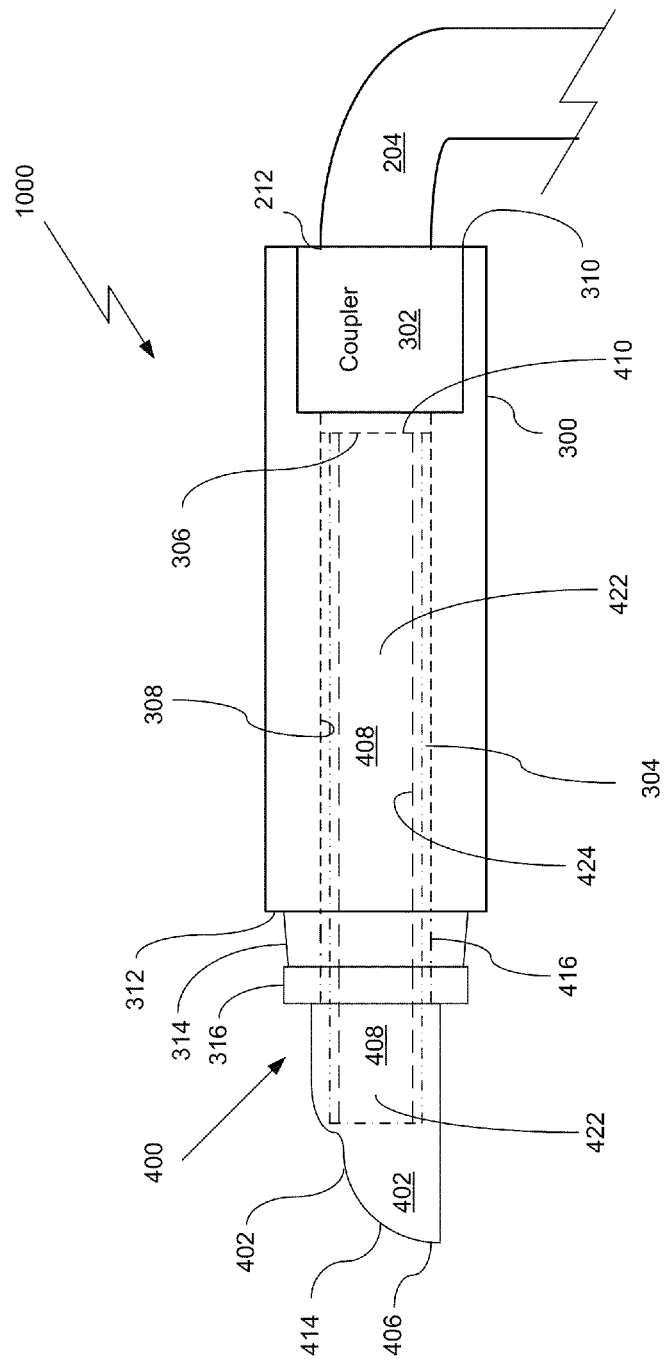
FIG. 10 is an assembly side view of an example of an implementation of the combination of the MISLH (shown in FIG. 3) and the MISLP (shown in FIG. 6) in accordance with the invention.

Turning to FIG. 10, an assembly 1000 side view is shown of an example of an implementation of the combination of the MISLH 300 (shown in FIG. 3) and the MISLP 400 (shown in FIG. 5) in accordance with the invention. In this example, the MISLP 400 has been inserted into the central bore 304 of the MISLH 300. The MISLP 400 is inserted by having the probe waveguide 408 snuggly inserted into the central bore 304 to a depth in the central bore 304 that places the probe waveguide distal end 410 in physical contact (i.e., adjoined) to the beam stop aperture 306. The beam stop aperture 306 is adjoined to the coupler 302. The probe sleeve 416 extends beyond the MISLH distal end 312 and is secured by the combination of collet 314 and nosepiece 316. The waveguide probe 408 includes the hollow lumen 422 that extends from the probe waveguide proximal end 410 to the probe waveguide distal end 412 and the lumen inner surface 424. The probe head 402 extends from the nosepiece 316 and includes the probe head distal end 406 and the scalloped portion 414.

In general, the MISLP 400 are designed with a common proximal waveguide configuration so that they may be interchangeably inserted into the MISLH 300, to a predefined depth, assuring that the laser energy delivered by the flexible hollow waveguide 204 is coupled into the probe waveguide 408 without needing any lenses. The MISLH 300 is designed to allow insertion of the probe waveguide 408 until it is butted up against the beam stop aperture 306. Features on each of the MISLP 400 and features inside the central bore 304 of the MISLH 300 insure that the probe waveguide 408 is inserted to a precisely controlled depth so the optimum energy coupling from the flexible hollow waveguide 204 into the probe waveguide 408 is achieved. The beam stop aperture 306 may be made from gold, or gold plated brass.

As an example of operation, the beam exits from the distal end 212 of the flexible hollow waveguide 204 where it has a narrow waist diameter that is in the center of the beam stop aperture 306 of about 500 microns. The beam waist is optically coupled into the proximal bore of the probe waveguide 408 where it continues to be conducted until it exits the probe tip 406. In this example, the beam stop aperture 306 also prevents any stray light energy from the "tails" of the Gaussian intensity profile from causing undesired heating of the fiber polymer cladding within the probe waveguide 408.

The MISLP 400 may also include a design where the acrylic sleeving at the probe waveguide distal end 412 of the probe waveguide 408 is removed for a distance of about 0.04 to 0.06 inches to prevent glass particle debris from being retained by the acrylic when the glass capillary is cleaved. The length of the probe waveguide 408 insertion into the MISLH 300 may be precisely defined by the position of the intermediate stainless sleeve and its distance from the proximal end of the probe waveguide 408 thereby insuring interchangeability for any specialized MISLP 400.

In an example of operation, a laser beam is transmitted from the flexible hollow waveguide 204 to coupler 302. The laser beam is them passed through the coupler 302 and beam stop aperture 306 to the probe waveguide 408. The probe waveguide 408 then passes and transmits the laser beam from the hollow lumen 422 at the probe waveguide distal end 412 which may focus to beam waist spot that may be located at a distance from the probe head distal end 406. Additionally, as an example of operation, a gas such as, for example, filtered air, another gas or gaseous mixture may be pumped through the hollow tube of the flexible hollow waveguide 204, the coupler 302, beam stop aperture 306, and hollow lumen (not shown) of the probe waveguide 408 to the probe head 402 so that the gas provides a means for clearing away smoke, or other debris, caused by the laser tissue ablation at the incision so as to give a surgeon a clear view of the cutting process.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A Minimally Invasive Surgical Laser Hand-piece ("MISLH") for use with a probe, where the MISLH has a MISLH proximal end and MISLH distal end, the MISLH comprising: an optical coupler located at the MISLH proximal end; a central bore within the MISLH; and an internal beam stop aperture within the central bore adjoined to the optical coupler, wherein the central bore extends from the optical coupler to the MISLH distal end, wherein the central bore is configured to accept the insertion of the probe within the central bore at the MISLH distal end, wherein central bore is configured to accept the insertion of the probe such that the probe is adjoined to the internal beam stop aperture, and wherein the probe is a Minimally Invasive Surgical Laser Probe ("MISLP") that includes a probe head that has a probe head proximal end and probe head distal end, and a probe waveguide that protrudes from the probe head proximal end, wherein the central bore is configured to accept the insertion of the probe waveguide within the central bore.

2. The MISLH of claim 1, wherein the probe waveguide includes a hollow flexible tube having a bore less than approximately 1.0 mm in diameter and having a smooth bore surface, a reflective layer disposed upon the surface of the bore, the exposed surface of which is approximately as smooth as the surface of the bore, and a dielectric film formed upon the exposed smooth surface of the reflective layer, the thickness of which is selected for a particular wavelength of infrared radiation, and having an exposed surface approximately as smooth as the surface of the reflective layer.

3. The MISLH of claim 2, wherein the dielectric film has an index of refraction that is less than the index of refraction of the reflective layer.

4. The MISLH of claim 1, wherein the probe waveguide is a waveguide for transmitting a plurality of co-axial beams of electromagnetic radiation from at least one radiation source, the probe waveguide including a hollow, flexible tube having a transparent annular body surrounding a bore with a smooth inner bore surface, and a reflective layer disposed upon the inner bore surface, wherein the bore transmits a first of said co-axial beams of electromagnetic radiation, and wherein the hollow, flexible tube transmits electromagnetic radiation from a second of said co-axial beams through its annular body.

5. The MISLH of claim 1, wherein the probe waveguide has a probe waveguide proximal end and a probe waveguide distal end, wherein the probe waveguide distal end corresponds to the probe head proximal end, and wherein the probe waveguide is configured to receive a laser beam input with a field pattern of radiation having a transverse electromagnetic mode ("TEM.sub.00") mode at the probe waveguide proximal end and, in response, produce an output laser beam with a TEM.sub.00 mode field pattern of radiation at the probe head distal end.

6. The MISLH of claim 5, wherein the optical coupler is configured to receive a laser beam MISLH input with a field pattern of radiation having a TEM.sub.00 mode.

7. The MISLH of claim 6, wherein the optical coupler is a Subminiature version A ("SMA") fiber optic connector.

8. The MISLH of claim 1, further including a collet located at the MISLH distal, and a nosepiece located at the MISLH distal adjacent to the collet, wherein the collet accepts the probe waveguide into the central bore and wherein therein the nosepiece is configured to tighten the collect to grip the inserted probe waveguide.

9. The MISLH of claim 8, wherein the optical coupler is a Subminiature version A ("SMA") fiber optic connector.

10. The MISLH of claim 1, wherein the central bore is configured to allow gas to travel through the central bore.

11. The MISLH of claim 10, wherein the probe is a Minimally Invasive Surgical Laser Probe ("MISLP") that include a probe head that has a probe head proximal end and probe head distal end, a probe waveguide that protrudes from the probe head proximal end, wherein the probe waveguide has a probe waveguide proximal end and a probe waveguide distal end, wherein the probe waveguide distal end corresponds to the probe head proximal end, and a hollow lumen that extends from the probe waveguide proximal end to the probe waveguide distal end, wherein the central bore is configured to accept the insertion of the probe waveguide within the central bore, wherein the central bore is configured to allow gas to travel through the central bore, and wherein the hollow lumen is configured to allow gas to travel through the hollow lumen.

12. A Minimally Invasive Surgical Laser Probe ("MISLP") for use with a Minimally Invasive Surgical Laser Hand-piece ("MISLH") having a central bore within the MISLH, the MISLP comprising: a probe head that includes a probe head proximal end and a probe head distal end; and a probe waveguide that protrudes from the probe head proximal end, wherein the probe waveguide is configured to be inserted within the central bore, wherein the probe waveguide includes a hollow flexible tube having a bore less than approximately 1.5 mm in diameter and having a smooth bore surface, a reflective layer disposed upon the surface of the bore, the exposed surface of which is approximately as smooth as the surface of the bore, and a dielectric film formed upon the exposed smooth surface of the reflective layer, the thickness of which is selected for a particular wavelength of mid-infrared radiation, and having an exposed surface approximately as smooth as the surface of the reflective layer.

13. The MISLP of claim 12, wherein the dielectric film has an index of refraction that is less than the index of refraction of the reflective layer.

14. The MISLP of claim 12, wherein the probe waveguide is a waveguide for transmitting a plurality of co-axial beams of electromagnetic radiation from at least one radiation source, the probe waveguide including a hollow, flexible tube having a transparent annular body surrounding a bore with a smooth inner bore surface, and a reflective layer disposed upon the inner bore surface, wherein the bore transmits a first of said beams of electromagnetic radiation, and wherein the hollow, flexible tube transmits electromagnetic radiation from a second of said beams through its annular body.

15. The MISLP of claim 12, wherein the probe waveguide has a probe waveguide proximal end and a probe waveguide distal end, wherein the probe waveguide distal end corresponds to the probe head proximal end, and wherein the probe waveguide is configured to receive a laser beam input with a field pattern of radiation having a transverse electromagnetic mode ("TEM.sub.00") mode at the probe waveguide proximal end and, in response, produce an output laser beam with a TEM.sub.00 mode field pattern of radiation at the probe head distal end.

16. The MISLP of claim 15, wherein the output laser beam at the probe head distal end has a Gaussian beam profile with a spot size that is minimum at a distance f from the probe waveguide distal end; and wherein the probe head has a length from the probe head proximal end to the probe head distal end that is approximately equal to the distance f.

17. The MISLP of claim 15, wherein the output laser beam at the probe head distal end has a Gaussian beam profile with a spot size that is minimum at a distance f from the probe waveguide distal end.

18. The MISLP of claim 12, wherein the probe waveguide has a probe waveguide proximal end and a probe waveguide distal end, wherein the probe waveguide distal end corresponds to the probe head proximal end, and a hollow lumen that extends from the probe waveguide proximal end to the probe waveguide distal end, wherein the hollow lumen is configured to allow gas to travel through the hollow lumen.

* * * * *